US00PP25053P2

(12) United States Plant Patent
Verwer

(10) Patent No.: US PP25,053 P2
(45) Date of Patent: Nov. 11, 2014

(54) ***DAHLIA* PLANT NAMED 'HDLE105'**

(50) Latin Name: *Dahlia hybrida*
Varietal Denomination: HDLE105

(71) Applicant: Aad W. M. Verwer, Lisse (NL)

(72) Inventor: Aad W. M. Verwer, Lisse (NL)

(73) Assignee: Verwer Dahlias BV, Lisse (NL)

( * ) Notice: Subject to any disclaimer, the term of this patent is extended or adjusted under 35 U.S.C. 154(b) by 16 days.

(21) Appl. No.: 13/815,887

(22) Filed: Mar. 15, 2013

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Kent L Bell
(74) *Attorney, Agent, or Firm* — C. A. Whealy

(57) ABSTRACT

A new and distinct cultivar of *Dahlia* plant named 'HDLE105', characterized by its compact, mounding and dense plant habit; serrated dark-colored leaves; freely flowering habit; daisy-type inflorescence form; large inflorescences with light yellow-colored ray florets; and good post-production longevity.

2 Drawing Sheets

Botanical designation: *Dahlia hybrida.*
Cultivar denomination: 'HDLE105'.

BACKGROUND OF THE INVENTION

The present invention relates to a new and distinct cultivar of *Dahlia* plant, botanically known as *Dahlia hybrida*, and hereinafter referred to by the name 'HDLE105'.

The new *Dahlia* plant is a product of a planned breeding program conducted by the Inventor in Lisse, The Netherlands. The objective of the breeding program is to create new compact container *Dahlia* plants that have dark-colored leaves, large inflorescences and good postproduction longevity.

The new *Dahlia* plant originated from an open-pollination in Lisse, The Netherlands in 2009 of a proprietary seedling selection of *Dahlia hybrida* identified as code number VD5-272, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Lisse, The Netherlands in 2010.

Asexual reproduction of the new *Dahlia* plant by cuttings since the spring of 2011 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'HDLE105'. These characteristics in combination distinguish 'HDLE105' as a new and distinct *Dahlia* plant:

1. Compact, mounding and dense plant habit.
2. Serrated dark-colored leaves.
3. Freely flowering habit.
4. Daisy-type inflorescence form.
5. Large inflorescences with light yellow-colored ray florets.
6. Good postproduction longevity.

Plants of the new *Dahlia* differ primarily from plants of the female parent selection in the following characteristics:

1. Plants of the new *Dahlia* are more compact and denser than plants of the female parent selection.
2. Leaves of plants of the new *Dahlia* are darker in color than leaves of plants of the female parent selection.
3. Plants of the new *Dahlia* and the female parent selection differ in ray floret color as plants of the female parent selection have reddish brown-colored ray florets.

Plants of the new *Dahlia* can be compared to plants of the *Dahlia hybrida* 'HDW79', disclosed in U.S. Plant Pat. No. 23,298. In side-by-side comparisons conducted in Lisse, The Netherlands, plants of the new *Dahlia* differed from plants of 'HDW79' in the following characteristics:

1. Plants of the new *Dahlia* were taller and broader than plants of 'HDW79'.
2. Plants of the new *Dahlia* were more freely branching and denser than plants of 'HDW79'.
3. Plants of the new *Dahlia* had thicker stems than plants of 'HDW79'.
4. Leaves of plants of the new *Dahlia* were lighter in color than leaves of plants of 'HDW79'.
5. Plants of the new *Dahlia* had larger inflorescences than plants of 'HDW79'.
6. Plants of the new *Dahlia* were more freely flowering than plants of 'HDW79'.
7. Plants of the new *Dahlia* and 'HDW79' differed in ray floret color as plants of 'HDW79' had white-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering plants of 'HDLE105' grown in an outdoor nursery.

The photograph on the second sheet is a close-up view of a typical flowering plant of 'HDLE105'.

DETAILED BOTANICAL DESCRIPTION

The photographs and following observations and measurements describe plants grown during the summer and autumn in ground beds in an outdoor nursery in Lisse, The Netherlands and under cultural practices typical of commercial *Dahlia* production. During the production of the plants, day temperatures ranged from 10° C. to 25° C. and night temperatures ranged from 5° C. to 20° C. Plants were pinched one time about three weeks after planting. Plants were 14 weeks old when the photographs and description were taken. In the following description, color references are made to The Royal Horticultural Society Colour Chart, 1995 Edition, except where general terms of ordinary dictionary significance are used.

Botanical classification: *Dahlia hybrida* 'HDLE105'.

Parentage:

*Female, or seed, parent*.—Proprietary seedling selection of *Dahlia hybrida* identified as code number VD5-272, not patented.

*Male, or pollen, parent*.—Unknown selection of *Dahlia hybrida*, not patented.

Propagation:

*Type*.—By vegetative cuttings.

*Time to initiate roots, summer*.—About eleven days at soil temperatures of 15° C.

*Time to initiate roots, winter*.—About 13 days at soil temperatures of 15° C.

*Time to produce a rooted young plant, summer*.—About 21 days at soil temperatures of 15° C.

*Time to produce a rooted young plant, winter*.—About 22 days at soil temperatures of 15° C.

*Root description*.—Fine, fleshy; white in color.

*Rooting habit*.—Moderately freely branching; dense.

*Tubers*.—Length: About 15 cm. Diameter: About 15 cm. Texture: Corky. Color: Close to 199B.

Plant description:

*Plant and growth habit*.—Compact and mounding plant habit; inverted triangular plant form; freely basal branching with about twelve lateral branches per plant; dense and bushy appearance; inflorescences held above the foliar plane on strong peduncles; vigorous growth habit.

*Plant height*.—About 35 cm.

*Plant diameter or spread*.—About 40 cm.

*Lateral branches*.—Length: About 22 cm. Diameter: About 1.8 cm. Internode length: About 6 cm to 11 cm. Texture: Smooth, glabrous. Strength: Strong. Color: Close to 146A tinted with close to 200C.

Leaf description:

*Arrangement*.—Opposite, single or compound with three or five leaflets.

*Leaf length*.—About 4.5 cm to 19 cm.

*Leaf width*.—About 2.5 cm to 9 cm.

*Shape*.—Ovate.

*Apex*.—Acuminate.

*Base*.—Attenuate.

*Margin*.—Serrate; sinuses divergent.

*Venation pattern*.—Pinnate.

*Texture, upper and lower surfaces*.—Smooth, glabrous.

*Color*.—Developing leaves, upper surface: Close to 137B. Developing leaves, lower surface: Close to or darker than 191A. Fully expanded leaves, upper surface: Close to 147A; venation, close to 183B. Fully expanded leaves, lower surface: Close to 191A; venation, close to 147A.

*Petioles*.—Length, all leaves and leaflets: About 2 mm to 20 mm. Diameter, all leaves and leaflets: About 2.5 mm. Texture, upper and lower surfaces: Smooth, glabrous. Color, upper surface: Close to 187B. Color, lower surface: Close to 148A.

Inflorescence description:

*Appearance and flowering habit*.—Rotate daisy-type inflorescences with ray and disc florets developing acropetally on a receptacle; inflorescences positioned above and beyond the foliar plane on strong peduncles; inflorescences face mostly upright; freely flowering habit with typically more than 100 inflorescences developing per plant.

*Fragrance*.—None detected.

*Time to flower*.—Plants begin flowering about 65 days after planting; flower continuously during the summer and autumn in The Netherlands.

*Post-production longevity*.—Good postproduction longevity; inflorescences maintain good substance for about 15 days on the plant and for about five days as a cut flower; inflorescences persistent.

*Inflorescence buds*.—Height: About 1.9 cm. Diameter: About 1.6 cm. Shape: Oblate. Color: Towards the base, close to 147A; mid-section, close to 152A; towards the apex, close to 180A.

*Inflorescence diameter*.—About 9.3 cm.

*Inflorescence depth* (*height*).—About 2.5 cm.

*Disc diameter*.—About 2.4 cm.

*Receptacle height*.—About 9 mm.

*Receptacle diameter*.—About 1.6 cm.

*Receptacle color*.—Close to 187B.

*Ray florets*.—Length: About 4.3 cm. Width: About 2.6 cm. Shape: Ovate. Apex: Rounded. Base: Attenuate. Margin: Entire. Aspect: Initially upright to roughly perpendicular to the peduncle. Texture, upper and lower surfaces: Smooth, glabrous; velvety. Number of ray florets per inflorescence: About eight arranged in a single whorl. Color: When opening, upper surface: Close to 2A. When opening, lower surface: Close to 2A; longitudinal ribs, close to 181B. Fully opened, upper surface: Close to 5A; color does not fade with development. Fully opened, lower surface: Close to 3C; longitudinal ribs, close to 183B.

*Disc florets*.—Shape: Tubular; apex dentate. Length: About 8 mm. Diameter: About 0.5 mm. Number of disc florets per inflorescence: About 95. Color, immature: Apex: Close to 17A. Mid-section: Close to 1B. Base: Close to 1C. Color, mature: Apex: Close to 17A. Mid-section and base: Close to 1C.

*Phyllaries*.—Quantity per inflorescence: About five arranged in a single whorl. Length: About 1.6 cm. Width: About 7 mm. Shape: Ovate. Apex: Acute. Base: Attenuate. Margin: Entire. Texture, upper and lower surfaces: Smooth, glabrous. Color, upper surface: Close to 200A. Color, lower surface: Close to or darker than 200A.

*Peduncles*.—Length, terminal peduncle: About 6 cm to 11 cm. Length, fourth peduncle: About 7 cm. Length, seventh peduncle: About 12 cm. Diameter: About 2.5 mm. Strength: Strong. Aspect: Mostly erect. Texture: Smooth, glabrous. Color: Close to 183B

*Reproductive organs*.—Androecium, present on disc florets only: Quantity per disc floret: Five. Filament length: About 4 mm. Filament color: Close to 3D. Anther shape: Lanceolate. Anther length: About 2 mm. Anther color: Close to 2C. Pollen amount: Abundant. Pollen color: Close to 23A. Gynoecium, present on ray and disc florets: Quantity per floret: One. Pistil length: About 4.5 mm. Stigma shape: Lanceolate. Stigma color: Close to 4C. Style length: About 2.5 mm. Style color: Close to 4C. Fruits: Length: About 2.2 cm. Diameter: About 1.9 cm. Texture: Smooth, glabrous. Color: Close to 187B. Seeds: Length: About 7 mm. Diameter: About 1 mm. Color: Close to 187B.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'HDLE105' as illustrated and described.

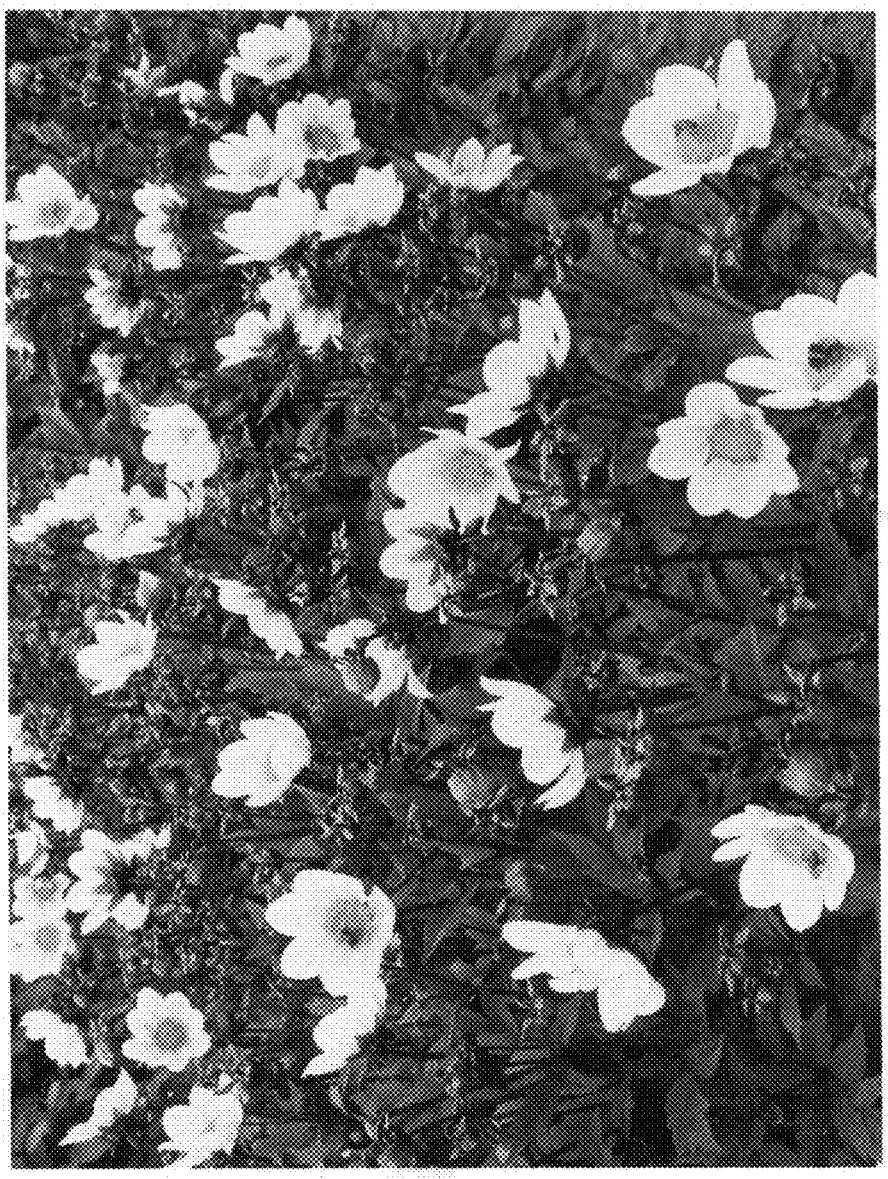

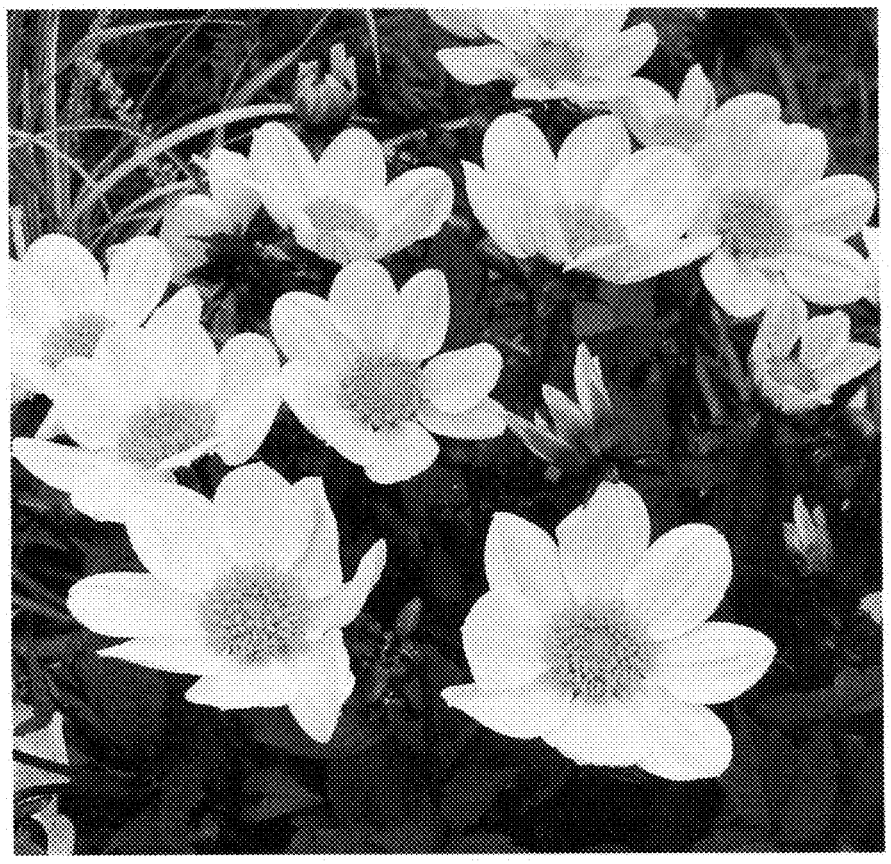

* * * * *